US012575884B2

(12) United States Patent
Erkamp et al.

(10) Patent No.: US 12,575,884 B2
(45) Date of Patent: Mar. 17, 2026

(54) ATHERECTOMY GUIDANCE THROUGH PHOTOACOUSTIC SIGNAL ANALYSIS

(71) Applicant: KONINKLIJKE PHILIPS N.V., Eindhoven (NL)

(72) Inventors: Ramon Quido Erkamp, Swampscott, MA (US); Alvin Chen, Cambridge, MA (US); Shyam Bharat, Arlington, MA (US); Mingxin Zheng, Cambridge, MA (US); Grzegorz Andrzej Toporek, Cambridge, MA (US); James David Cezo, Colorado Springs, CO (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 528 days.

(21) Appl. No.: 18/009,127

(22) PCT Filed: Jun. 15, 2021

(86) PCT No.: PCT/EP2021/066081
§ 371 (c)(1),
(2) Date: Dec. 8, 2022

(87) PCT Pub. No.: WO2021/255013
PCT Pub. Date: Dec. 23, 2021

(65) Prior Publication Data
US 2023/0225793 A1 Jul. 20, 2023

Related U.S. Application Data

(60) Provisional application No. 63/040,564, filed on Jun. 18, 2020.

(51) Int. Cl.
*A61B 18/24* (2006.01)
*A61B 18/00* (2006.01)

(52) U.S. Cl.
CPC .... *A61B 18/24* (2013.01); *A61B 2018/00577* (2013.01)

(58) Field of Classification Search
CPC ..................... A61B 18/24; A61B 2018/00577
See application file for complete search history.

(56) References Cited

U.S. PATENT DOCUMENTS 7,050,692 B2    5/2006  Harlan
7,549,985 B2    6/2009  O'Donnell
        (Continued)

FOREIGN PATENT DOCUMENTS

WO    WO-2019152789 A1 *   8/2019  ........... A61B 5/6852

OTHER PUBLICATIONS

International Search Report and Written Opinion Dated Sep. 23, 2021 For International Application No. PCT/EP2021/066081 Filed Jun. 15, 2021.
(Continued)

*Primary Examiner* — Benjamin J Klein
*Assistant Examiner* — Thien Jason Tran

(57) ABSTRACT

Methods, Apparatuses, and Systems of operating a laser atherectomy system to perform an endoscopic atherectomy procedure within a vessel at a therapeutic region of an anatomical condition by use of an atherectomy laser device coupled to an ultrasound imaging probe. The atherectomy laser device operates to generate photoacoustic signals from a light source of the atherectomy laser device to for guidance within the vessel and to characterize tissue about the therapeutic region by delivery of pulsed wavelengths within the vessel, and to perform operations of tissue ablation directed to the anatomical condition. This enables guidance of the atherectomy laser device by feedback from the viewing of photoacoustic images based on photoacoustic signals generated the atherectomy laser device and created in response
(Continued)

to changes in acoustic intensity due to changes of optical wavelength monitored by the ultrasound imaging probe.

17 Claims, 11 Drawing Sheets

(56)                    References Cited

U.S. PATENT DOCUMENTS

| | | | |
|---|---|---|---|
| 7,572,254 | B2 | 8/2009 | Hebert |
| 9,907,614 | B2 | 3/2018 | Grace |
| 2008/0108867 | A1 | 5/2008 | Zhou |
| 2009/0227997 | A1 | 9/2009 | Wang |
| 2015/0359595 | A1 | 12/2015 | Ben |
| 2017/0112384 | A1 | 4/2017 | Maswadi |
| 2019/0076124 | A1* | 3/2019 | Subhash .............. A61B 5/0088 |

OTHER PUBLICATIONS

Johnson, et al: "All optical extravascular laser-ultrasound and photoacoustic imaging of calcified atherosclerotic plaque in excised carotid artery", Jami L J et al., Photoacoustics, 9, 2018, pp. 62-72.

Laird, et al: "Limb salvage following laser-assisted angioplasty for critical limb ischemia: results of the LACI multicenter trial", J Endovasc Ther. 2006;13:1.

"Eximo Medical's B-Laser Atherectomy System Successfully Used to Cross CTOs Without a Guidewire", Endovascular Today, May 12, 2019.

Luminus, SST-90-R Product Datasheet, 2015.

"Laser Atherectomy in Peripheral Arterial Disease", Apr. 2007, Cath Lab Digest https://www.cathlabdigest.com/articles/Laser-Atherectomy-Peripheral-Arterial-Disease.

Wang, et al: "Intravascular Photoacoustic Imaging", IEEE J Quantum Electron. Jun. 3, 2010; 16(3): 588-599.

Anderson, et al: "Selective photothermolysis of lipid-rich tissues: A free electron laser study", Lasers Surg Med. 2006;38:913-919.

Ho, et al: "Intima-Media Thickness of Lower-Limb Arteries Associated with Fasting and Post-Challenge Plasma Glucose Levels", Journal of Atherosclerosis and Thrombosis vol. 16, No. 6.

Unawali, et al: "Deep 3D convolutional neural network for automatic cancer tissue detection using multispectral photoacoustic imaging", Proceedings vol. 10955, Medical Imaging 2019: Ultrasonic Imaging and Tomography; 109551D (2019).

Van Den Berg, et al: "Feasibility of photoacoustic/ultrasound imaging of synovitis in finger joints using a point-of-care system", Photoacoustics, vol. 8, Dec. 2017, pp. 8-14.

Scott Prahl: "Optical Absorption of Hemoglobin", 1999.

Scott Prahl: "Optical Absorption of Indocyanine Green (ICG)", 2018.

* cited by examiner

Catheter pulled
back and rotated

50
Optical exit

Philips turbo laser atherectomy procedure

Catheter
retreated

De bulking
different region

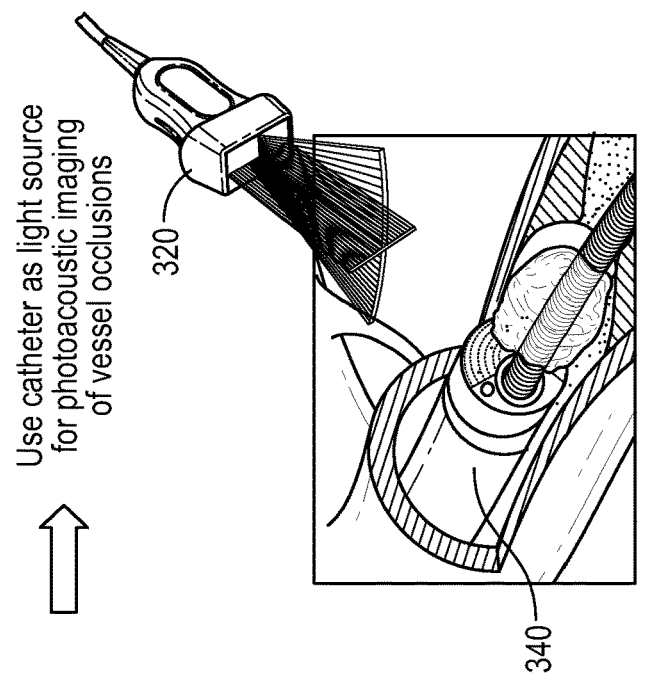

Use catheter as light source
for photoacoustic imaging
of vessel occlusions

320

340

Solves tissue light attenuation problem larger depths
Creates information about plaque composition
Receive only beamforming allows for high frame rate

FIG. 3B

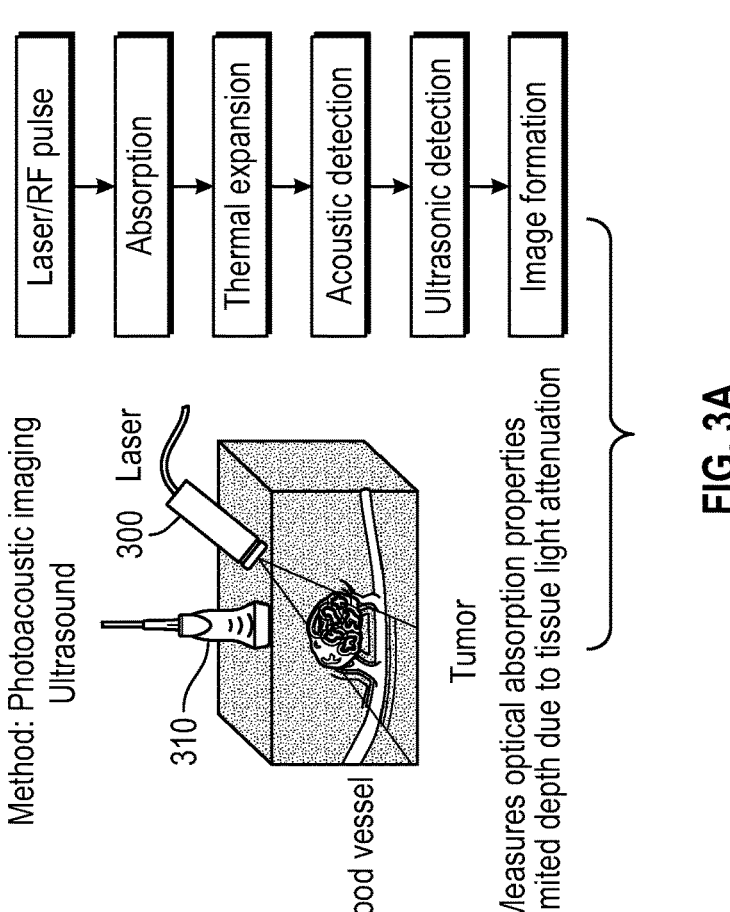

Laser/RF pulse → Absorption → Thermal expansion → Acoustic detection → Ultrasonic detection → Image formation Method: Photoacoustic imaging
Ultrasound 300  Laser

310

Blood vessel

Tumor

Measures optical absorption properties
limited depth due to tissue light attenuation

FIG. 3A

Optical absorption spectra for vascular relevent tissue types

Closing the loop
to laser:
Modulate intensity
to intervenionalist / robot:
push speed
rotation
saline flush
Are we done?

Use ultrasound imaging probe
Get high SNR signals
Characterize plaque/ calcium
Detect vessel wall Therapy feedback
Laser intensity
push speed
Device rotation
Are we done?

Vascular
3D probe
(XL14-3 xMATRIX)

630

620

600

610

900

1100

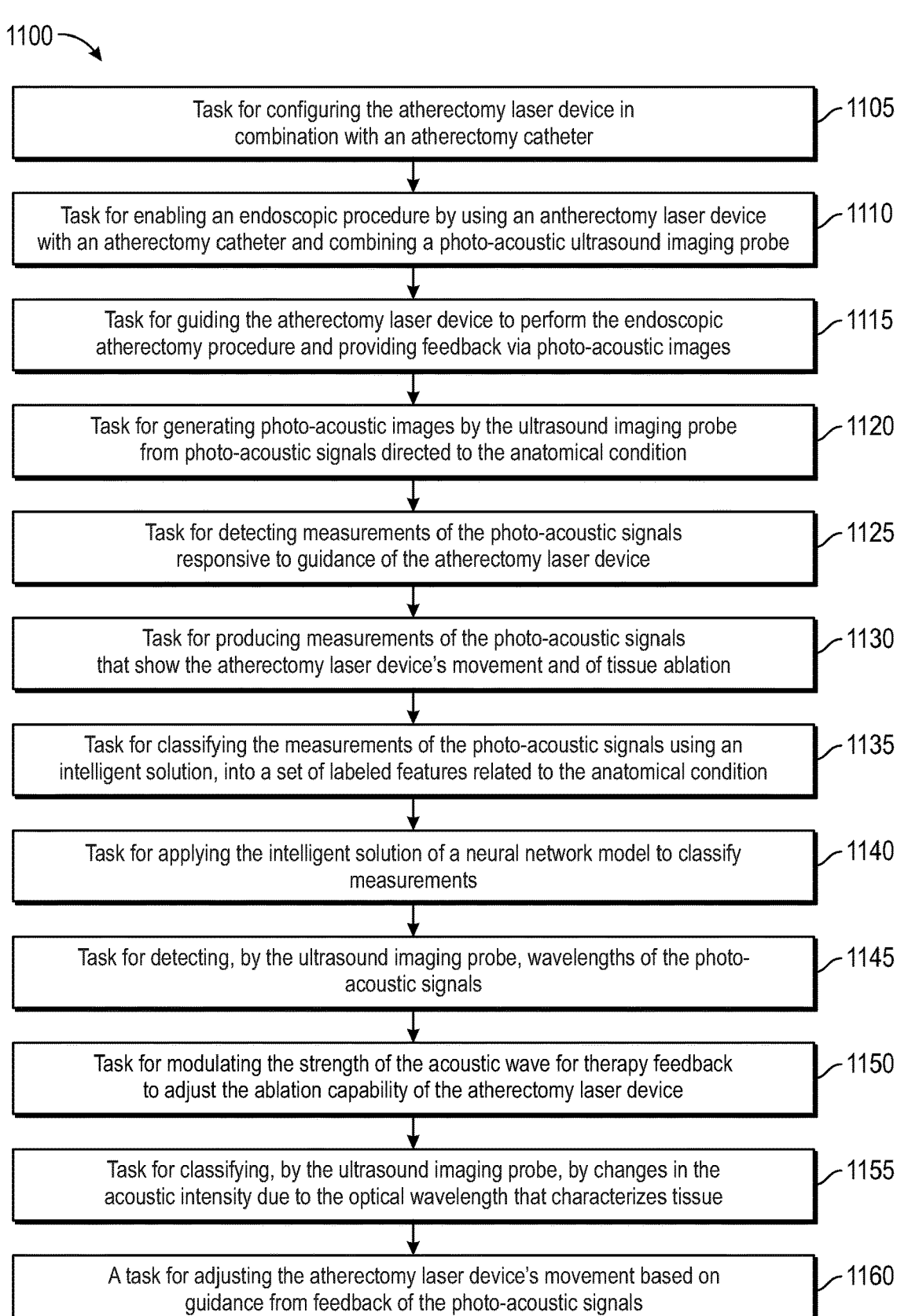

Task for configuring the atherectomy laser device in combination with an atherectomy catheter — 1105

Task for enabling an endoscopic procedure by using an antherectomy laser device with an atherectomy catheter and combining a photo-acoustic ultrasound imaging probe — 1110

Task for guiding the atherectomy laser device to perform the endoscopic atherectomy procedure and providing feedback via photo-acoustic images — 1115

Task for generating photo-acoustic images by the ultrasound imaging probe from photo-acoustic signals directed to the anatomical condition — 1120

Task for detecting measurements of the photo-acoustic signals responsive to guidance of the atherectomy laser device — 1125

Task for producing measurements of the photo-acoustic signals that show the atherectomy laser device's movement and of tissue ablation — 1130

Task for classifying the measurements of the photo-acoustic signals using an intelligent solution, into a set of labeled features related to the anatomical condition — 1135

Task for applying the intelligent solution of a neural network model to classify measurements — 1140

Task for detecting, by the ultrasound imaging probe, wavelengths of the photo-acoustic signals — 1145

Task for modulating the strength of the acoustic wave for therapy feedback to adjust the ablation capability of the atherectomy laser device — 1150

Task for classifying, by the ultrasound imaging probe, by changes in the acoustic intensity due to the optical wavelength that characterizes tissue — 1155

A task for adjusting the atherectomy laser device's movement based on guidance from feedback of the photo-acoustic signals — 1160

FIG. 11

ATHERECTOMY GUIDANCE THROUGH PHOTOACOUSTIC SIGNAL ANALYSIS

CROSS REFERENCE TO RELATED APPLICATIONS

This application is the U.S. National Phase application under 35 U.S.C. § 371 of International Application No. PCT/EP2021/066081 filed Jun. 15, 2021, which claims the benefit of U.S. Provisional Patent Application No. 63/040,564 filed Jun. 18, 2020. These applications are hereby incorporated by reference herein.

TECHNICAL FIELD

Embodiments of the subject matter described herein relate generally to medical devices, and more particularly, embodiments of the subject matter relate to methods, apparatuses, and systems for imaging of biological tissue by collecting real-time streaming data from laser atherectomy therapy characterizing the biological tissues around a therapeutic region with an analysis of photoacoustic signals produced.

BACKGROUND

Traditional ultrasound creates an image showing the acoustic properties of tissue and has limited ability to differentiate between tissue types with different chemical compositions. This tissue differentiation becomes more challenging as the structures get smaller and are further away from the probe surface.

Endovascular interventions have been successfully employed to treat peripheral arterial diseases (PAD). However, no clear consensus has been reached regarding optimal treatment modality. The current mainstay of endovascular therapy for lower extremity PAD consists of balloon angioplasty. Laser atherectomy is a process that can be used to enable crossing through chronic total occlusions (CTO) via a wire.

However, there are drawbacks to this process as there is a need to quantify calcium severity and plaque burden in arteries during the laser atherectomy. Hence to facilitate this process with more visual guidance, and this is especially desirable during CTO crossings without prior guidewire crossing performed in a procedure. To overcome this guidance obstacle, x-rays have been used, but x-ray images do not show soft tissue contrasts that are needed for guiding the atherectomy laser in a vessel. Further, it has been established that vessel and occlusion visualization are beneficial to help clinicians direct at what locations further ablation is required that can result in better procedure outcomes.

Therefore it is desired for visual images of the CTO occlusion when trying to cross the CTO with a laser atherectomy catheter without having to rely on the presence of a prior crossed guidewire. This kind of visual guidance loop in the therapy, can also prevent vessel wall punctures, avoid other complications that can be caused. For example, such complications may include improper saline flushing and can make the debulking or cytoreductive surgical (CRS) with the laser easier to perform.

It is desirable to implement methods, and systems to combine an external ultrasound imaging probe placed in a photoacoustic imaging mode with use of a laser atherectomy system which can be configured with multiple pulsed wavelengths for use and have a trigger line configured from the atherectomy system to the external ultrasound imaging probe to generate photoacoustic images for monitoring and providing feedback of the progress of the laser atherectomy procedure based on photoacoustic signals generated by the laser atherectomy device.

It is desirable to implement methods and systems of a laser atherectomy system that enables the combining of the ultrasound imaging probe functionality with the laser atherectomy system for imaging of localizations in biological tissue and collecting real-time streaming data of the progress of the laser atherectomy therapy by characterizing the biological tissues around a therapeutic region from acoustic signals produced by the atherectomy laser device with an analysis for feedback to assist in the guidance of the atherectomy laser device.

The above information disclosed in this Background section is only for enhancement of understanding of the background of the invention and therefore it may contain information that does not form the prior art that is already known in this country to a person of ordinary skill in the art.

SUMMARY

Disclosed herein are methods and systems of combining the ultrasound imaging probe functionality with the laser atherectomy system for imaging of within a vessel and localization in biological tissue by collecting real-time streaming data from laser atherectomy therapy characterizing the biological tissues around a therapeutic region with an analysis of photoacoustic signals directed at the localization or within the vessel for providing feedback via photoacoustic images from the ultrasound imaging probe for controlling the laser atherectomy device with a catheter used.

In accordance with an aspect of the present invention, a method of operating a laser atherectomy system is provided. The method includes performing an endoscopic atherectomy procedure within a vessel at a therapeutic region of an anatomical condition by use of an atherectomy laser device in combination with an ultrasound imaging probe, the atherectomy laser device operating to generate a plurality of photoacoustic signals from a light source of the atherectomy laser device about the therapeutic region by delivery of pulsed wavelengths within the vessel at the therapeutic region, and to perform operations of tissue ablation directed to the anatomical condition; and guiding the atherectomy laser device operating within the vessel with feedback provided by photoacoustic images which are generated by the ultrasound imaging probe based on a plurality of photoacoustic signals that have been generated by the atherectomy laser device while the atherectomy laser device is operating at the therapeutic region for the anatomical condition.

In various exemplary embodiments, the method includes configuring the atherectomy laser device with a primary light source and a secondary light source wherein the primary light source is used for performing the tissue ablation and the secondary light source is used for generating photoacoustic signals for the photoacoustic images.

The method further includes in response to an atherectomy laser device's movement in the vessel to within a close distance to the anatomical condition, automatically switching from a B-mode displaying a broader field of view (FOV) of the therapeutic region to a photoacoustic mode displaying a narrower FOV of the therapeutic region. The photoacoustic mode's narrower FOV displays a region including a close-up area of an atherectomy laser device's catheter tip within the vessel for providing a detailed display of different anatomical features within the vessel.

The method further includes overlaying an image generated in the photoacoustic mode on an image generated in the B-mode wherein the overlaid photoacoustic image is smaller in size than a B-mode image and configured about the close-up area of the atherectomy laser devices' catheter tip. The overlaid image can be enabled or disabled during the atherectomy procedure and wherein the overlaid image can be interleaved between enablement of the photoacoustic and B-mode. The method includes generating, by the laser atherectomy device, photoacoustic signals of multiple wavelengths of light by the secondary light source for creating a plurality of acoustic waves in a volume near the catheter tip within the vessel to distinguish tissue types by monitoring of the ultrasound imaging probe. The method includes in response to acoustic waves for different optical wavelengths emanating from the volume near the catheter tip and received by the ultrasound imaging probe, displaying, at a display device in communication with the ultrasound imaging probe, a set of photoacoustic images including photoacoustic images with a set of labels of different anatomical features at the therapeutic region wherein the set of labels are classified using an intelligent solution based on an acoustic wavelength that includes: a vessel wall, liquid blood, amounts of calcium, and composition of the plaque within the vessel; and in response to the labeled different anatomical features generated in the small volume around the atherectomy laser devices' catheter tip, providing a display about the orientation of a catheter in a vessel lumen.

In another exemplary embodiment, a laser atherectomy apparatus is provided. The apparatus includes an atherectomy laser device coupled to an ultrasound imaging probe to perform an endoscopic atherectomy procedure within a vessel at a therapeutic region for an anatomical condition by use of an atherectomy laser device; the atherectomy laser device configured to perform a first function using a primary light source to perform tissue ablation for the anatomical condition, and a second function using a secondary light source to generate a plurality of photoacoustic signals for one or more pulsed optical wavelengths within the vessel at the therapeutic region; and a display coupled to the atherectomy laser device to display photoacoustic images based on the photoacoustic signals generated by the atherectomy laser device's secondary light source to provide user guidance of the atherectomy laser device by display of photoacoustic images of the atherectomy laser device operating within the vessel and tissue about the atherectomy laser device within the vessel at the therapeutic region.

The apparatus further includes in response to an atherectomy laser device's movement in the vessel to within a close distance to the anatomical condition, the atherectomy laser device configured to enable an automatic switch from a B-mode of the display of displaying a broader field of view (FOV) of the therapeutic region to a photoacoustic mode of the display for displaying a narrower FOV of the therapeutic region. The apparatus includes the display coupled to the atherectomy laser device configured to display for the photoacoustic mode's narrower FOV of a region including a close-up area of an atherectomy laser device's catheter tip within the vessel to provide a detailed display of different tissue types within the vessel for visual guidance of the atherectomy laser device. The apparatus further includes the display configured to overlay an image generated in the photoacoustic mode on an image generated in the B-mode wherein the overlaid photoacoustic image is smaller in size than a B-mode image and configured about the close-up area of the atherectomy laser devices' catheter tip. The overlaid image can be enabled or disabled during the endoscopic atherectomy procedure. The apparatus includes the laser atherectomy device configured to generate photoacoustic signals of multiple wavelengths of light by the secondary light source for creating a plurality of acoustic waves for the different optical wavelengths in a volume near the atherectomy laser devices' catheter tip within the vessel to distinguish tissue types. The apparatus includes in response to acoustic waves for the different optical wavelengths that emanate from the volume near the catheter tip and are received by the ultrasound imaging probe, the display device in communication with the ultrasound imaging probe, configured to display a set of photoacoustic images including photoacoustic images with labels of different anatomical features at the therapeutic region wherein the labels are classified using an intelligent solution based on photoacoustic signals received by the ultrasound probe for different optical wavelengths. The set of labels includes a vessel wall, liquid blood, amounts of calcium, and composition of the plaque within the vessel. The apparatus further includes in response to the labeled anatomical features generated in the small volume around the catheter tip, providing a display about the orientation of a catheter in the vessel lumen.

In yet another exemplary embodiment, an atherectomy system is provided. The system includes a laser atherectomy device coupled with an ultrasound imaging probe and configured with a primary light source and a secondary light source to perform an atherectomy procedure by using the primary light source for tissue ablation of an anatomical condition at a therapeutic region discovered in the atherectomy procedure, and a second function by using a secondary light source to generate a plurality of photoacoustic signals of one or more pulsed optical wavelengths within the vessel at the therapeutic region which is monitored by the ultrasound imaging probe for creating photoacoustic images based on acoustic waves emanating from photoacoustic signals; and a display coupled to the atherectomy laser device, to display the photoacoustic images wherein the photoacoustic signals are generated by the atherectomy laser device's secondary light source and provide user guidance by viewing of the display presenting the photoacoustic images in real-time of operations of an atherectomy laser device's movement and tissue ablation within the vessel at the therapeutic region during the atherectomy procedure.

In various exemplary embodiments, the atherectomy system further includes in response to the atherectomy laser device's movement in the vessel to within a close distance to the anatomical condition, the display configured to automatically switch from a display in a B-mode of the ultrasound imaging probe to display a broader field of view (FOV) of the therapeutic region to a display in a photoacoustic mode of the ultrasound imaging probe to display a narrower FOV of the therapeutic region. The display coupled to the atherectomy laser device displaying the photoacoustic mode's narrower FOV of a region including a close-up area of an atherectomy laser device's catheter tip to provide a detailed display of different tissue types within the vessel for visual guidance of the atherectomy laser device. The atherectomy system further includes, the display further configured to: overlay an image generated in the photoacoustic mode on an image generated in the B-mode wherein the overlaid photoacoustic image is substantially smaller than a B-mode image and configured about the close-up area of the atherectomy laser devices' catheter tip. The atherectomy system further includes the laser atherectomy device configured to generate photoacoustic signals of multiple wavelengths of light by the secondary light source to create a plurality of acoustic waves for the different optical wavelengths in a volume near the atherectomy laser devices' catheter tip within the vessel for receipt by the ultrasound imaging probe to create photoacoustic images with labels of different tissue types wherein the labels are classified using an intelligent solution based on acoustic wavelengths.

The above advantage and other advantages and features of the present disclosure will be apparent from the following detailed description of the preferred embodiments when taken in connection with the accompanying drawings.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures, which may be illustrated for simplicity and clarity and are not necessarily drawn to scale.

FIGS. 3A and 3B depict exemplary photoacoustic imaging compared to a catheter-based photoacoustic imaging system of the laser atherectomy system in accordance with one or more exemplary embodiments;

FIG. 11 is an exemplary flowchart of the endoscopic procedure for operating the laser atherectomy system in accordance with one or more exemplary embodiments.

Figures 1A, 1B, 1C, 1D, 1E:
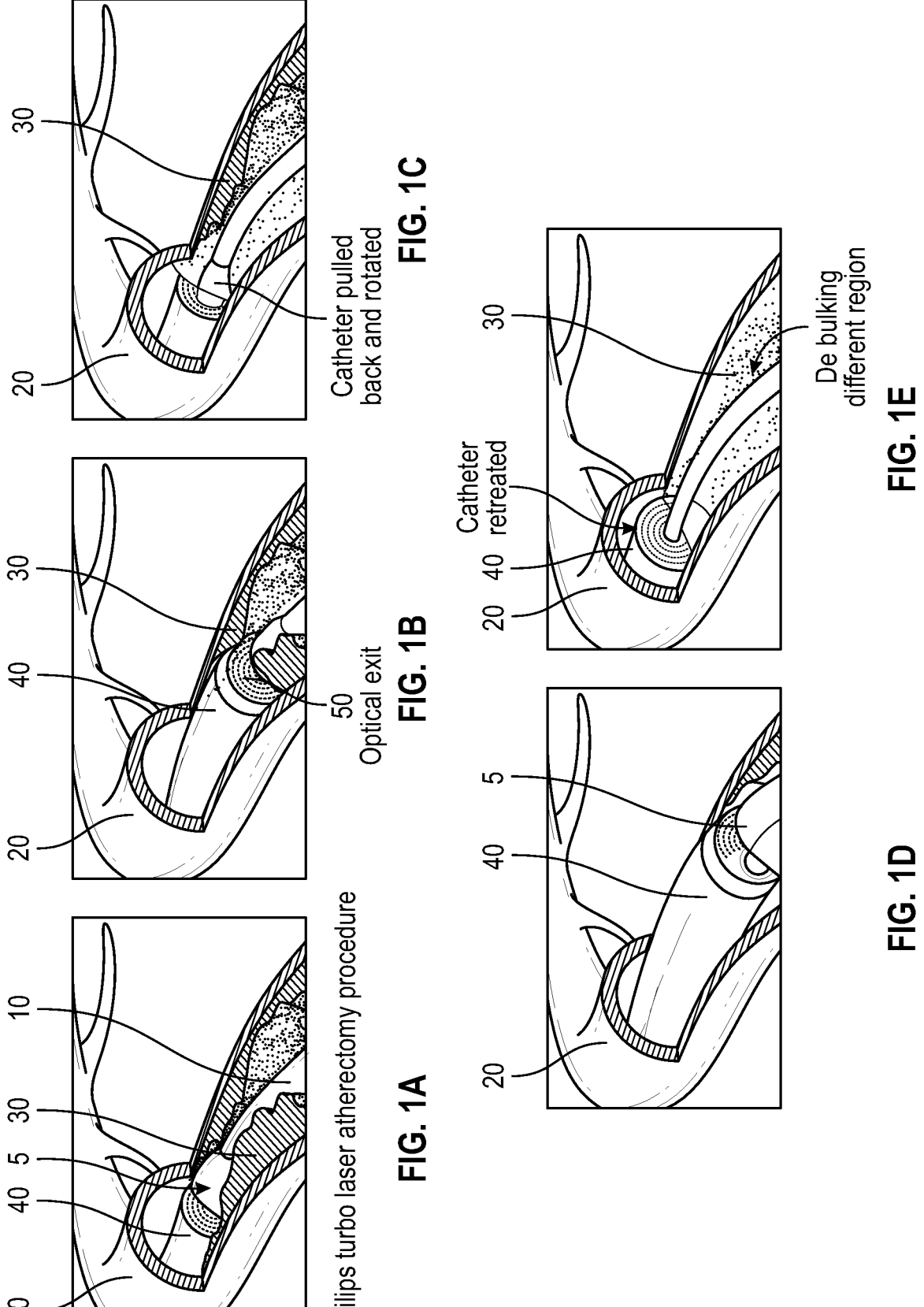
FIGS. 1A, 1B, 1C, 1D, and 1E depict a series of steps of an exemplary laser atherectomy procedure in which a laser atherectomy device is used for ablating tissue within the cardiovascular system of a subject in accordance with one or more exemplary embodiments.

The above-mentioned and other features and advantages of this invention, and the manner of attaining them, will become more apparent and the invention will be better understood by reference to the following description of embodiments of the invention taken in conjunction with the accompanying drawings.

The exemplifications set out herein illustrate preferred embodiments of the invention, and such exemplifications are not to be construed as limiting the scope of the invention in any manner.

DETAILED DESCRIPTION

Embodiments of the present disclosure are described herein. It is to be understood, however, that the disclosed embodiments are merely examples and other embodiments can take various and alternative forms. The figures are not necessarily to scale; some features could be exaggerated or minimized to show details of particular components. Therefore, specific structural and functional details disclosed herein are not to be interpreted as limiting but are merely representative. The various features illustrated and described with reference to any one of the figures can be combined with features illustrated in one or more other figures to produce embodiments that are not explicitly illustrated or described. The combinations of features illustrated provide representative embodiments for typical applications. Various combinations and modifications of the features consistent with the teachings of this disclosure, however, could be desired for particular applications or implementations.

While the subject matter described herein can be implemented in the form of medical devices, such as laser atherectomy catheter that captures ultraviolet light for treating multiple lesion morphologies within PAD lesions. For the sake of brevity, conventional techniques related to laser atherectomy catheter system operation, and other functional aspects of the systems (and the individual operating components of the systems) may not be described in detail here. Examples of laser atherectomy catheters may be of the type described in, but not limited to, U.S. Pat. Nos. 9,907,614; 7,050,692 and 7,572,254; each of which is herein incorporated by reference.

Peripheral artery disease (PAD) is characterized by clogged or obstructed arteries in the lower extremities. The Center for Disease Control (CDC) in published statistics has indicated that approximately upwards of 8 million people in the United States have PAD, including a large percentage in the vicinity of 12-20% of seniors over 60 years old. PAD is caused by a build-up of plaque in the arteries carrying blood to the head, organs, and limbs. The built-up plaque is composed of fibrous tissue, fat, cholesterol, calcium, and other substances. The built-up plaque in time has been shown to stiffen and cause narrowing of the arteries, limiting the flow of oxygen-rich blood to the affected body parts affecting a person's health. For example, the PAD most commonly affects the blood flow in the legs and to organs such as the brain, arms, kidneys, and stomach. The diagnosis of PAD can be based on a combination of tests such as a physical exam, ankle-brachial index, ultrasound, angiography, and blood tests. If PAD is detected early and still in a mild stage, the disease may be managed with lifestyle changes (quit smoking, diet, exercise) and medications (lowering blood pressure or cholesterol, blood thinners).

In the case, of more advanced cases of PAD with higher amounts of plaque built up, such cases require and are treated with surgical interventional procedures to manage the blockages inpatient's vessels. For example, in some patients' angioplasty procedures can be performed that widen the blocked vessel through an inflatable balloon, and this balloon procedure is often combined with stent placement to support the vessel and to keep it open. Such cases may also be suitable for atherectomy procedures. In this case, the atherectomy procedure is performed through a surgical catheter that physically removes the blockage by use of mechanical abrasion or optical energy deposition at the locality of the blockage that can result in an opening of the blocked vessel.

The excimer laser angioplasty procedure is similar in some respects to conventional coronary balloon angioplasty. A narrow, flexible tube, the laser catheter, is inserted into an artery in the arm or leg. The laser catheter contains one or more optical fibers, which can transmit laser energy. The laser catheter is then advanced inside the artery to the targeted obstruction at the desired treatment site. After the laser catheter has been positioned, the laser is energized to "remove" the obstruction.

The present disclosure describes various exemplary embodiments that provide systems and processes for combining an external ultrasound imaging probe enable in a photoacoustic imaging mode, a laser atherectomy system that is enabled with two or more pulsed wavelengths, a trigger line from the atherectomy system to the ultrasound system, and a photoacoustic image processing system, to monitor a laser atherectomy procedure by imagery produced from the pulsed wavelengths of the laser atherectomy system.

The present disclosure describes systems and methods combining an external ultrasound imaging probe and a laser atherectomy device for generating feedback responsive to an analysis of photoacoustic signals directed at the localization (i.e. therapeutic region) that can be produced with audible and visual alerts for the clinician that is responsive to movement of the laser atherectomy system and anatomical conditions encountered by the laser atherectomy device and the atherectomy catheter during the endoscopic atherectomy procedure. For example, this may include, photoacoustic signal responsive to the laser atherectomy device movement towards the vessel wall tissue, liquid blood in the vessel, and ablation operations of calcium (plaque) deposits forming the localization within the vessel.

The present disclosure describes systems and methods where for multiple optical wavelengths photoacoustic signals are generated by the atherectomy laser device, to provide feedback of the ablation operations of the laser atherectomy device in the vessel, and are analyzed by an intelligent solution to provide enhanced photoacoustic visual representations of the endoscopic atherectomy procedure at the locality in the vessel for better control of the laser atherectomy device by the clinician. Also, the present disclosure describes add-ons to an existing or legacy laser atherectomy systems to enable the enhance photoacoustic visual functionalities and feedback analysis through the convenient adding of optional add-on modules.

The present disclosure describes systems and methods to deliver laser therapy and characterize the tissues around the therapeutic region based on the same action by photoacoustic signals generated at the therapeutic region providing feedback of the tissue removal and movement of the atherectomy laser device. In an exemplary embodiment, additional feedback of the like can be also achieved by the adding of at least one or more secondary light sources to an existing or next-generation type laser atherectomy system. For example, in an exemplary embodiment, the PHILIPS® Excimer laser atherectomy system can be modified with additional light sources. Also, an intelligent solution for analysis of the photoacoustic signals at the localization using an artificial intelligence model such as a neural network can be implemented. The neural network can be used to analyze multiple photoacoustic signals generated in response to a range of optical wavelengths from the laser atherectomy device in the vessel which is monitored by an extravascular ultrasound probe during the atherectomy procedure. The photoacoustic signals provide feedback about the therapeutic effect caused by the clinician (i.e. user) control of the laser atherectomy device and atherectomy catheter performing the procedure in real-time. The ability of the clinician to treat and monitor (e.g. in instances both simultaneously or to monitor alone) the treatment outcomes in real-time via photoacoustic images generated enables the implementation of closed-loop mechanisms for controlling the atherectomy laser action in the vessel.

FIGS. 1A-1E illustrate a set of steps of an exemplary laser atherectomy procedure in which a laser atherectomy device is used for use in ablating tissue in interventional procedures within the cardiovascular system of a subject. FIGS. 1A-1E illustrate the laser atherectomy procedure to facilitate a crossing by using a "step-by-step" technique in which the guidewire 10 is advanced just proximal to the lesion 30 (such as a chronic total occlusion (CTO)), and the excimer laser catheter is advanced to the cap for use to penetrate the fibrous cap (<5 mm distance). Then the guidewire 10 is advanced again in the lesion 30 until the guidewire 10 cannot go further; then the excimer laser is used again to penetrate the lesion 30. These steps (in FIGS. 1A-1E) are repeated until the lesion 30 is crossed. In FIG. 1A, a guidewire 10 is inserted in a vessel 20 across a lesion 30. Then the atherectomy catheter 40 of the laser atherectomy device 5 is inserted by a user (i.e. clinician) over the guidewire 10 and advanced to the start of the lesion 30. In FIG. 1A, at the first step ("Step A"), the particular type of rotational position is selected. Then in FIG. 1B, in the second step ("step B"), the atherectomy catheter 40 is again slowly advanced and the laser of the laser atherectomy device 5 is initiated to evaporate the material that is directly in front of the optical exit aperture 50. The 308 nm UV wavelength of the atherectomy device 5 has a typical absorption depth of about 50μ, and each pulse of the excimer laser removes only a portion of the tissue (about 10μ of tissue). The atherectomy catheter 40 then continues as guided by the guidewire 10 with a slow advancement speed of about 0.5 mm per second. Next, in FIG. 1C, the third step ("Step C"), the catheter is pulled back and rotated to point at the next desired treatment area. Then, the fourth step ("Step D") shows the catheter being advanced again to debulk a different area, and in FIG. 1E ("step E") the atherectomy catheter is retracted and the debulked area from the second pass is illustrated. The procedure is performed in the catheter-lab, and during the ablation (removal of the tissue by the laser), a constant slow saline flush is used to prevent blood and x-ray contrast agents positioned in front of the optical exit aperture 50 as both elements can interfere with lesion ablation and tissue removal. In the atherectomy procedure, x-ray imaging can be made available, however, it is preferably not used for guidance atherectomy catheter during the ablation process as imaging from the x-ray does not provide visualization of the soft tissue in the procedure locality, and the x-ray contrast medium cannot be used during the ablation as it will interfere with the optical exit aperture 50 and laser removal. Therefore, the procedure guidance is mainly through tactile feedback and a properly placed guidewire that prevents the atherectomy catheter from deviating significantly from a correct vessel path.

Hence, the laser Atherectomy has been also used to facilitate the crossing of the wire through chronic total occlusions (CTO). As a CTO is a complete occlusion it cannot be visualized on an x-ray because the contrast agent is not able to penetrate the lesion. This lack of X-ray guidance can make it impossible to safely cross the lesion with a guidewire.

Further, the laser atherectomy procedure is more effective when the artery is straight. This is because, in tortuous arteries, it is difficult to maintain the catheter position and perform a step-by-step technique (e.g. illustrated in FIGS. 1A-1E), as this can lead to a catheter exit extravascular. For example, the two main complications that are exhibited in this procedure are perforation, that can result if a particular segment of the vessel is a tortuous configured segment and the atherectomy catheter is pushed too hard (i.e. the clinician applies a greater force to overcome the tortuous segment) to advance the catheter, the result that occurs is that the atherectomy catheter may penetrate a vessel wall potentially causing the perforation. The other complication is that if an appropriate technique is not used with the continuous cold saline flush, then there can be a high risk for dissection. The present disclosure also enables a basis for a second next-generation adaptation where the laser is merged with visualization with the laser catheter to allow better imaging within the vessel to determine where the ablation is required.

In the laser atherectomy, a catheter is maneuvered through the vessel until it reaches the blockage. Laser energy is used to essentially vaporize the blockage inside the vessel. The result is increased blood flow to the peripheral tissue.

Figures 2A, 2B, 2C:
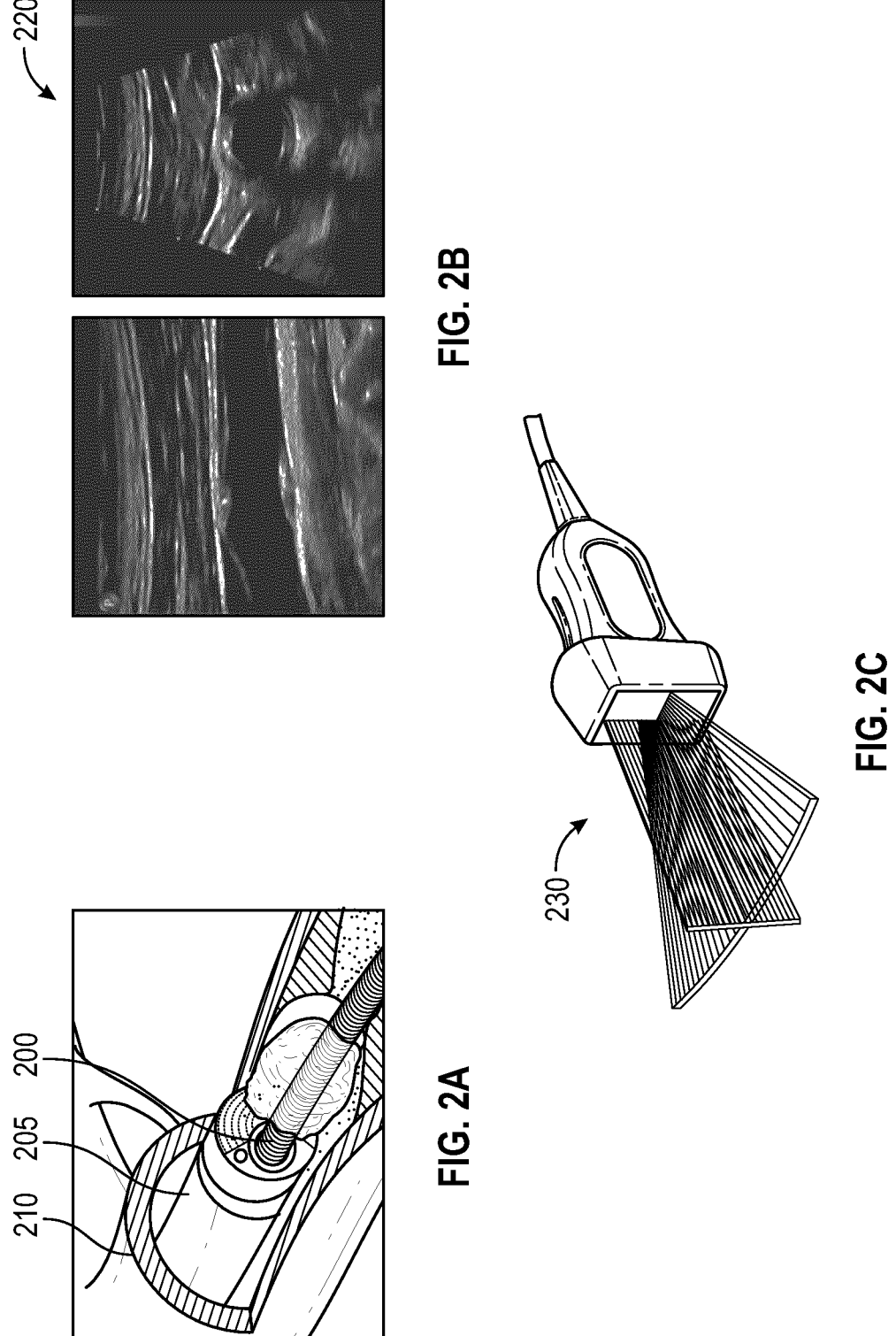
FIGS. 2A, 2B, and 2C illustrate and an external ultrasound imaging with the ability to visualize soft tissue contrast during the atherectomy procedure in accordance with one or more exemplary embodiments.

FIGS. 2A, 2B, and 2C illustrate and an external ultrasound imaging with the ability to visualize soft tissue contrast during the atherectomy procedure in accordance with various embodiments. The external ultrasound imaging can visualize soft tissue contrast during the atherectomy procedure. An exemplary ultrasound imaging probe for vascular assessment is the PHILIPS® XL14-3 xMATRIX linear array transducer with 3D/4D visualization for producing photoacoustic images. The PHILIPS® XL14-3 xMA-TRIX also can visualize anatomy in 3D/4D with an icon-driven menu workflow. The clinician can view directly into a vessel to evaluate plaque spatial location and composition, as well as 3D flow data to assess stenotic or torturous conditions in the vessel. Additionally, telemetry coupling may also be enabled with the ultrasound imaging probe for remote viewing by a remotely located viewer or clinician. In FIG. 2A, a diagram of an exemplary laser atherectomy device 200 and atherectomy catheter 205 is depicted in a vessel 210 performing a directional laser atherectomy. FIG. 2B depicts a 3D/4D visualization generated via the photoacoustic imaging probe. FIG. 2C depicts an exemplary photoacoustic imaging probe 230 that is used in conjunction with the atherectomy laser device 200 and atherectomy catheter 205 in the endoscopic atherectomy procedure.

FIGS. 3A and 3B depict exemplary photoacoustic imaging compared to a catheter-based photoacoustic imaging system. In FIG. 3A, an ultrasound probe 310 is illustrated with use with a laser 300. In this case, the ultrasound device 310 creates an image showing acoustic properties of the tissue with limited ability to differentiate between tissue types with different chemical compositions. This tissue differentiation becomes more challenging as the structures are reduced in size (i.e. gets smaller) or is positioned further away from the ultrasound probe 310 surfaces.

The primary interests in laser atherectomy process are determining what tissue type is right in front of the optical aperture (i.e. what tissue type is being ablated), and what is the position of the optical aperture relative to the vessel structure (what part of the vessel structure is the laser ablating). With the photoacoustic mode added to the ultrasound imaging device, the tissue type at the distal end where the optical aperture is located can be more easily differentiated and distinguished with the vessel wall.

In FIG. 3A, the photoacoustic imaging system transmits light pulses from laser unit 300 (light transmission aperture is often integrated into ultrasound probe housing through a fibreoptic pathway) that can advance through the tissue to the region of interest. When the light propagates in the tissue it attenuates quickly due to both scattering and absorption. Therefore the light source requires very high intensity and even with the highest safe intensity levels only up to 4 cm imaging depth can be achieved. At the region of interest, optical absorption takes place, leading to thermal expansion and the associated photoacoustic signal that can be received by the ultrasound probe. In FIG. 3B, in contrast, the catheter is used as the (secondary) light source and directs the pulsed laser light directly to the region of interest. This avoids large amounts of optical attenuation from the tissue, which allows for much better SNR with lower light intensity. The absorbed light energy creates heat leading to a very rapid thermal expansion of the tissue near the tip of the catheter. This expansion creates an acoustic wave, and the original location of this wave can be detected (which is the situs of the localization) using the ultrasound photoacoustic (imaging) probe that is enabled in a mode to receive via beamforming reception to detect the photoacoustic signals for the different optical wavelengths. The photoacoustic image can be formed from the beamforming reception by the ultrasound imaging probe and this indicates the distribution of light absorption and thermal expansion properties within the tissue. Using select wavelengths the optical absorption dependency on wavelength can be measured and used to uniquely identify specific tissue types.

Further, in FIG. 3B, in the laser atherectomy system, the light can be directly delivered to the area of interest using the optical fibers in the atherectomy catheter 340. Because the light only has to propagate a few millimeters at most, a much lower intensity light source is required and much higher SNR than in conventional photoacoustic imaging can be achieved. Longer wavelengths (IR) can be used to assess tissues in the vessel within a few millimeters from the tip. The UV wavelength of the ablation system has very high tissue absorption and will generate a photoacoustic signal exactly at the location where ablation takes place. Thus this wavelength can be used for tip/therapy location tracking, while the addition of other wavelengths allows characterization of tissue type at the therapy location.

Figures 4A, 4B:
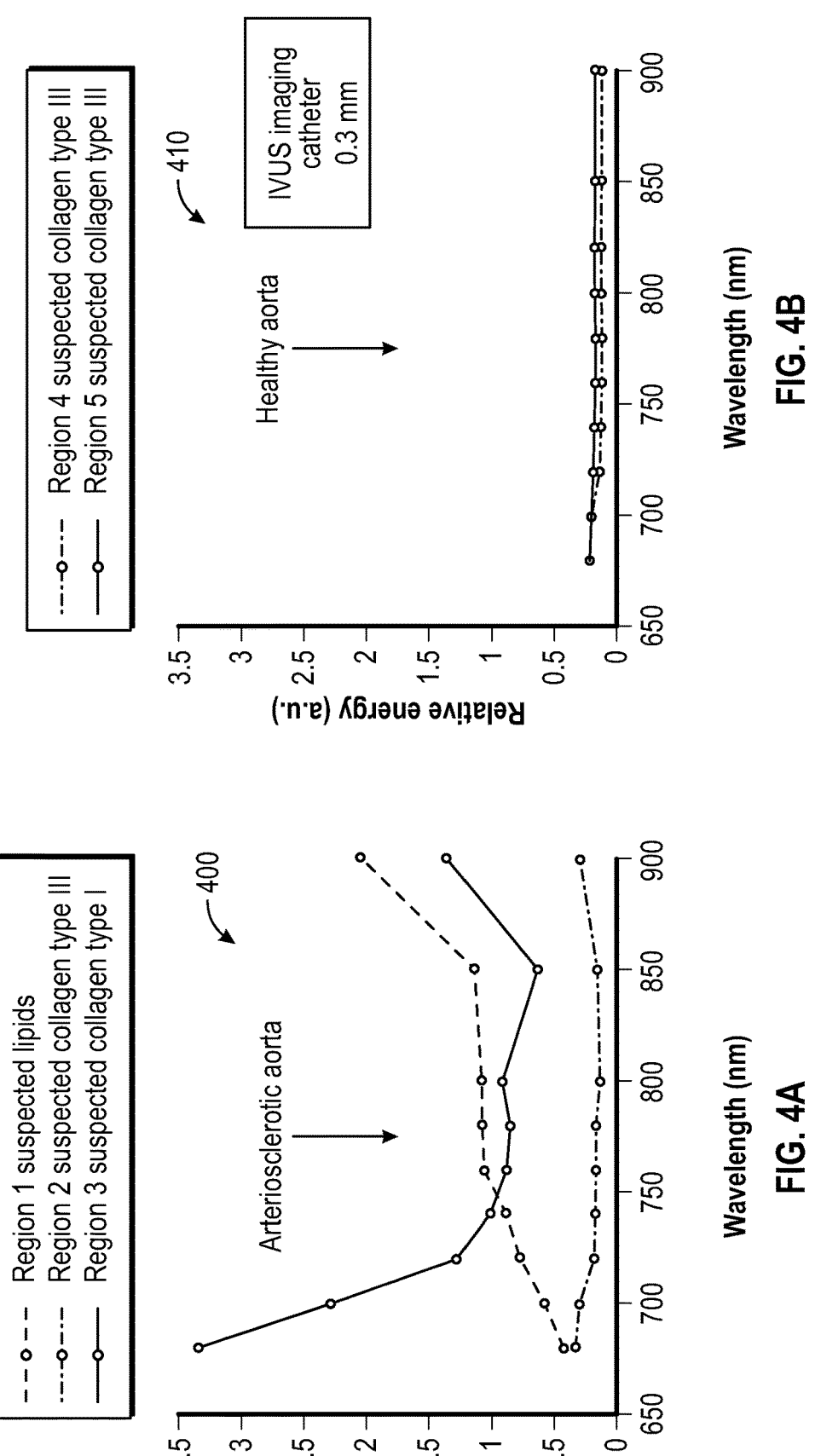
FIGS. 4A and 4B depict graphs of the occlusion characterization using photoacoustic imaging of the laser atherectomy system in accordance with one or more exemplary embodiments.

FIGS. 4A and 4B depict graphs of the occlusion characterization using photoacoustic. In the graph 400 of FIG. 4A photoacoustic imaging is performed in both a healthy aorta and an atherosclerotic aorta. FIG. 4B shows the ultrasound imaging performed with an intravascular imaging catheter used in the endoscopic procedure. The light is applied through a fiber attached alongside the catheter. The light source is a tunable pulsed laser, and the photoacoustic response is measured in 5 different regions. While 5 different regions are measured, it is contemplated that the number can be expanded or decreased as desired for measuring the photoacoustic response. That is, a variety of tissue types can be distinguished, monitored, and observed via photoacoustic images by a clinician for determinations of the healthy and arteriosclerotic aorta and to improve the outcome of the laser atherectomy procedure.

Figure 5:
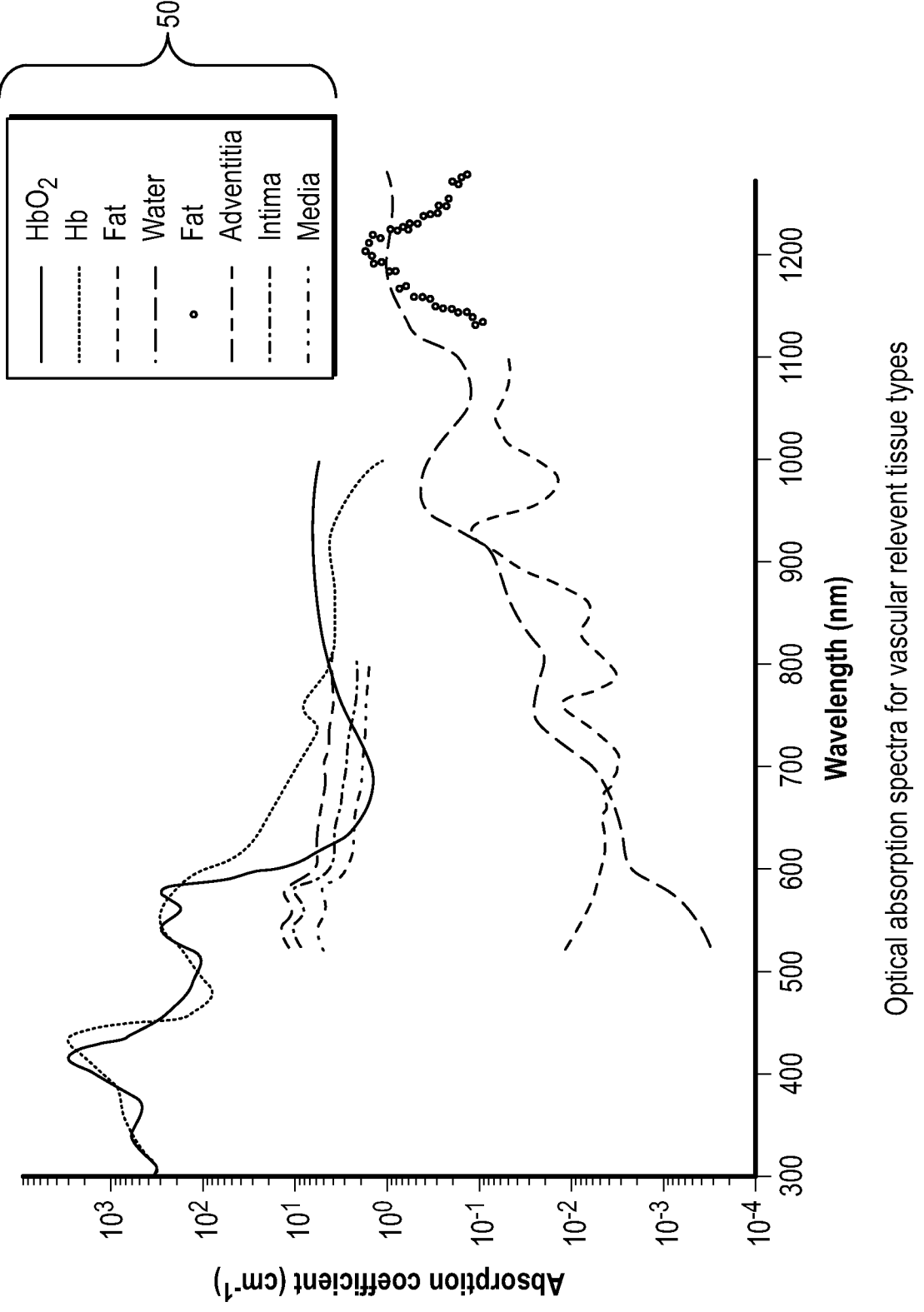
FIG. 5 depicts an optical absorption spectra for vascular relevant tissue types to differentiate a number of tissue types of the laser atherectomy system in accordance with one or more exemplary embodiments.

FIG. 5 depicts an optical absorption spectra for vascular relevant tissue types 500 to differentiate many tissue types. The optical absorption spectra for a range of relevant tissue types can be measured and compared in other group types of tissue as desired. In FIG. 5, at increasing wavelengths, the absorption coefficients are compared for optical absorption spectra for various types of vascular tissue and are distinguished in absorption graph comparisons.

Figure 6:
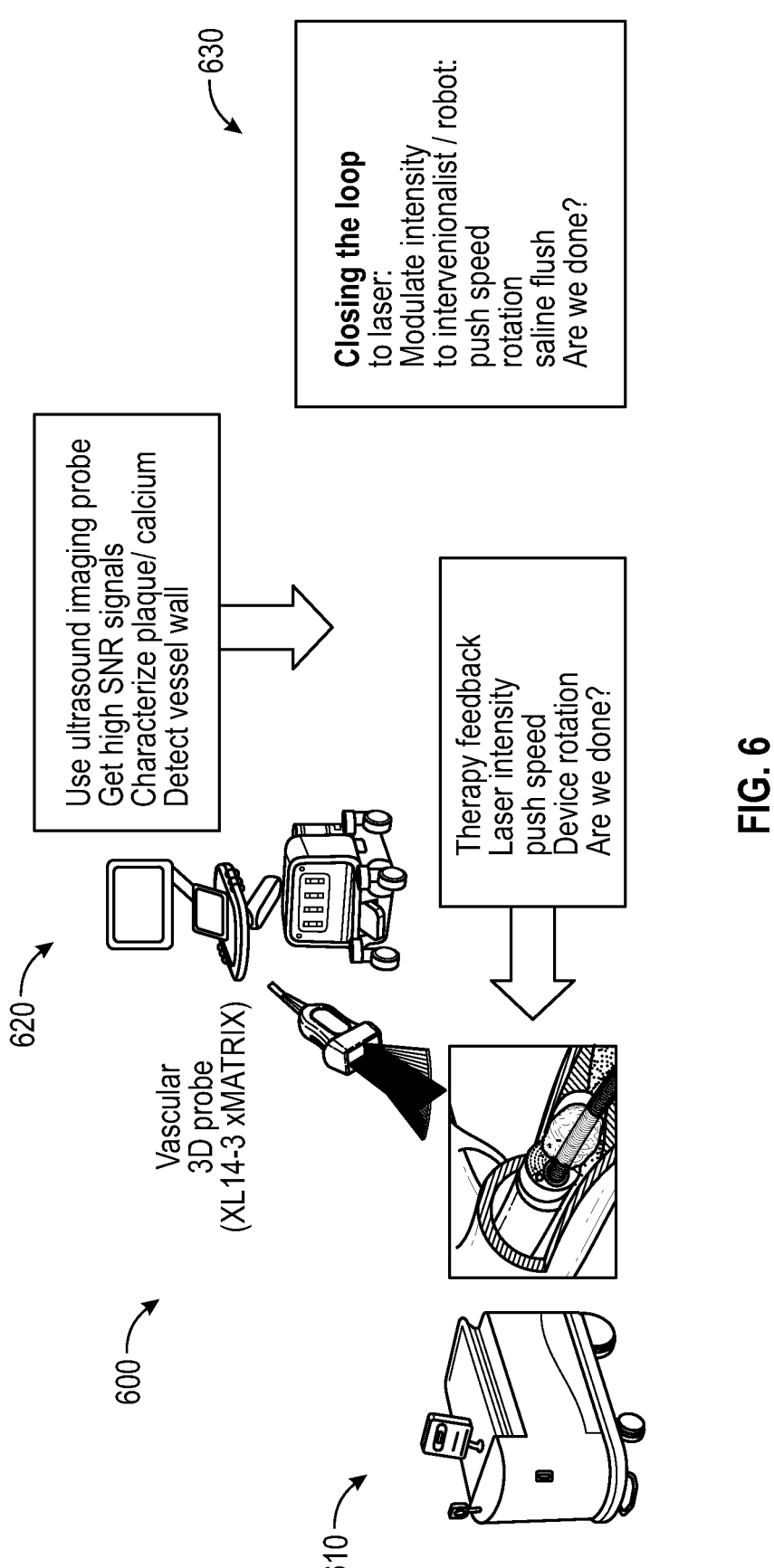
FIG. 6 depicts an exemplary laser atherectomy laser device and photoacoustic probe system for monitoring and analysis of photoacoustic signal for an endoscopic laser atherectomy procedure of the described laser atherectomy system in accordance with one or more exemplary embodiments.

FIG. 6 depicts an exemplary laser atherectomy laser device and photoacoustic probe system for monitoring and analysis of photoacoustic signal for an endoscopic laser atherectomy procedure of the described laser atherectomy system. In an exemplary embodiment, the ablation (with the primary light source) can be performed with a PHILIPS® TURBO-POWER™ laser atherectomy catheter that is connected to a modified CVX-300™ medical laser system. The atherectomy laser system described is modified to be able to provide additional low power light pulses (via the secondary light source) at several different wavelengths and to allow modulation of output power with an external control signal. The ablation process is monitored with an XL14-3™ matrix linear array connected to an EPIQ® ultrasound system. This array is optimized for vascular imaging and can provide volumes or high-resolution 2D frames with steerable orientation in 3D space. The software in the EPIQ® is modified to also add a photoacoustic small 3D volume mode where the transmit beam is suppressed and beamformer delay calculations are adjusted for receive only beamforming.

The photoacoustic signal is enabled or controlled to emanate only from a small volume around the tip of the atherectomy catheter. This is because the photoacoustic 3D volume mode required for the analysis can be performed with only a required small volume of photoacoustic signals that are needed to be captured. The required small volume of photoacoustic signals can be found and are centered around the distal tip of the photoacoustic imaging probe to capture each light wavelength of interest to differentiate the tissue in the vessel. From the photoacoustic signals which are generated at the tip location, and collected promptly, the movement of the tip direction can be determined (i.e. the direction of the atherectomy laser device). Also, the dynamics of the movement with the tip direction can be monitored via the photoacoustic images produced. This type of photoacoustic tip tracking allows us to select the proper orientation of the B-mode plane that should be visualized next. Thus there is an alternating acquisition sequence between b-mode and photoacoustic. Also, the photoacoustic acquisition can be done in a short time because one way directional sound traverse time is a reduced time (i.e. half the time) and there are little if any transmit beams to cycle through to fully use the entire range of the 32× beamformer, and the volume captured of the photoacoustic signal can be maintained at a small amount to generate the results.

In an exemplary embodiment, the ability to integrate at least two wavelengths into next-generation PHILIPS® laser system is illustrated in the PHILIPS® CVX-300™ and PHILIPS® NEXCIMER® laser systems where each can be configured to utilize both a UV laser (treating tissue) and secondary low-power red laser (a visible indicator of successful connection to the system). Having two or more light sources coupled into the same catheter is already built into the existing optics of the exemplary laser system. The modular add-on of additional sources both from a system design standpoint and regulatory therefore can easily be implemented. The NEXCIMER® Laser System may also be configured to accommodate future modifications. The hardware components of the exemplary laser systems are designed in a modular manner with additional slots available for the addition of new modules. Also, future additions to the NEXCIMER® Laser System can be enabled to expand the functionality of the atherectomy laser system. For example, in exemplary embodiments, added communication features and modules can be add-ons to exemplary PHILIPS® imaging systems such as C-arms, ultrasound systems, etc., The add-ons may be validated individually without having to fully validate the entire system.

The exemplary atherectomy laser device can be implemented in a modular system configuration with an add-on to the core system, e.g. as an upgrade to existing systems out in the field or a premium add-on that couples the laser system with photoacoustic ultrasound imaging probe. The module can be designed to be independent of the base laser function (UV light generation and delivery) and would or may fit within an existing enclosure.

Figure 7:
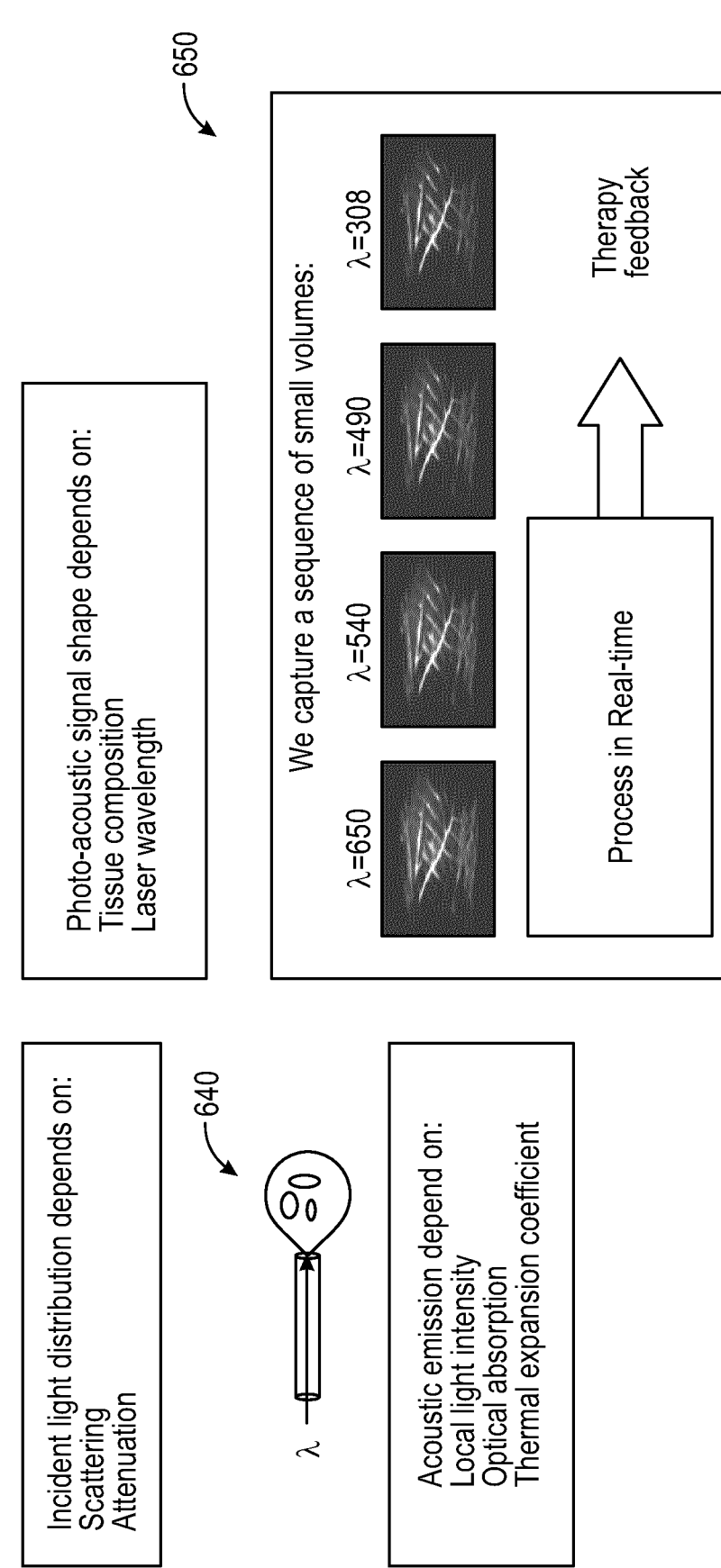
FIG. 7 depicts the solution of a photoacoustic characterization as a pattern recognition problem in accordance with one or more exemplary embodiments.

FIG. 7 depicts the solution 600 of a photoacoustic characterization as a pattern recognition problem. The vascular 3D imaging probe 610 generates a photoacoustic signal for display 620 of the characterization of the plaque and detecting of the vessel wall. The acquired photoacoustic signal consists of a sequence of small volumes of acoustic signals that need to be processed with low latency to provide timely therapy feedback 630. The feedback 630 can consist of the "closing the loop" to the atherectomy laser that entails modulating the intensity of the atherectomy laser, adjusting the push speed, and rotation and performing the saline flush. For example, the user may need to detect the presence of the vessel wall and switch off the ablation laser before the vessel wall is punctured. The rate of ablation is about 0.5 mm per second (via the primary light source). As an example, the largest vessel found in the leg, the common femoral artery has an intima-media thickness (IMT) of 0.66 mm. In order not to penetrate the vessel wall, the ablation laser must be switched off within a spacing of the vessel wall of about 660 ms for preventing about 50% of the vessel wall from removal by the laser ablation. The posterior tibial artery has IMT of 0.44 mm and therefore requires system latency less than 440 ms.

The incident light for the photoacoustic signal 640 is dependent on various properties including light scattering and attenuation. The distribution of the light, in this case, exiting the optical aperture of the catheter depends on both the scattering properties and attenuation properties of the tissue. The acoustic emission in each location depends on the local light intensity, how much of that local light gets absorbed, and the thermal expansion coefficient at that location. This causes the photoacoustic signal shape of the photoacoustic signal 640 to be dependent on the tissue composition, and this shape also changes depending on the wavelength of the light pulse. Thus a specific tissue type will give rise to a unique sequence of volumetric patterns. A sequence of small volumes 650 of various wavelengths 650, 640, 490, and 308 that can be captured and processed in real-time for therapeutic feedback.

Figure 8:
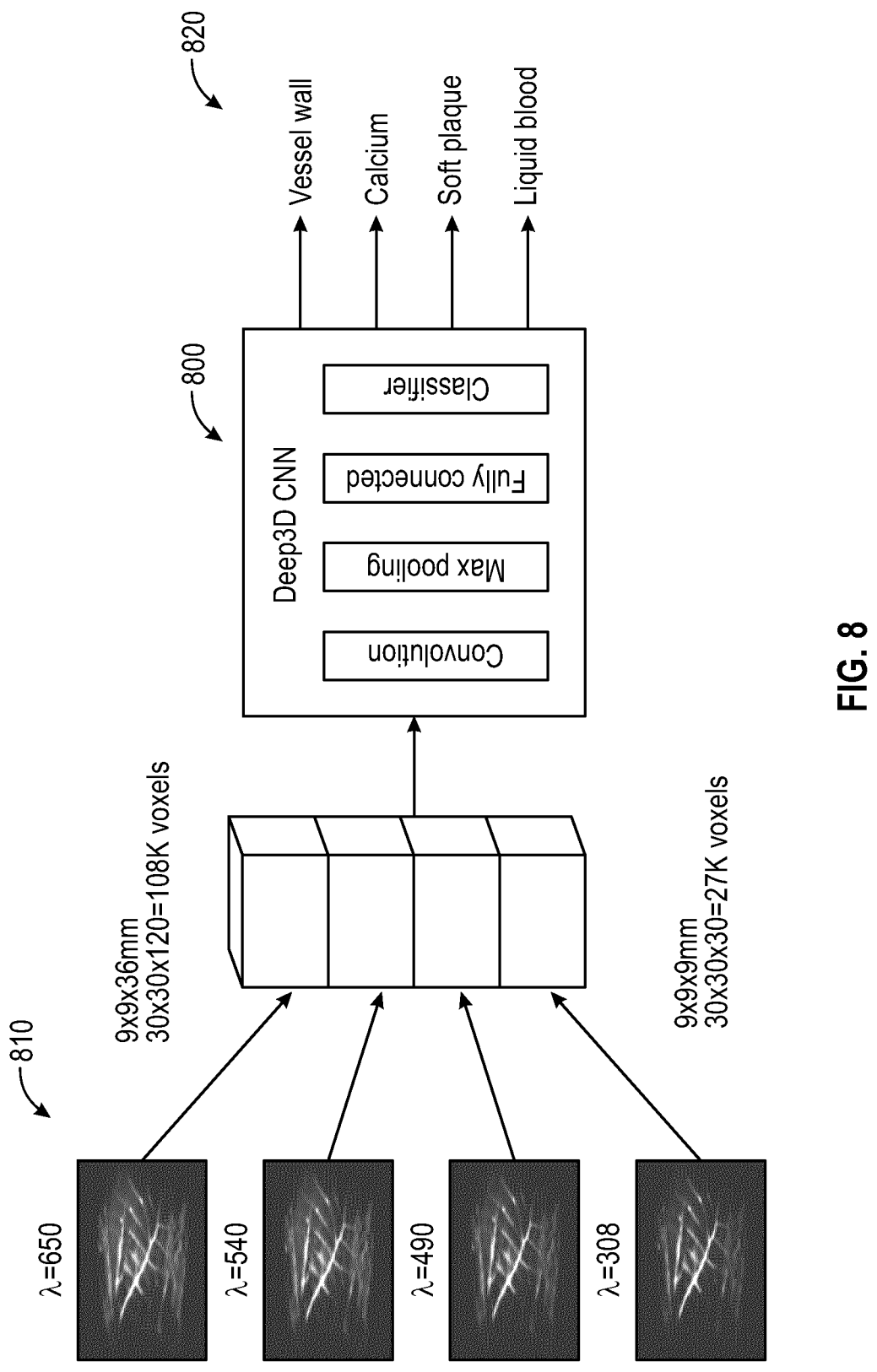
FIG. 8 depicts a 3D convolutional neural network (CNN) for atherectomy tissue classification in accordance with one or more exemplary embodiments in accordance with one or more exemplary embodiments.

FIG. 2 depicts a 3D convolutional neural network (CNN) for atherectomy tissue classification in accordance with various embodiments. The 3D CNN 800 is configured with 4 binary classifiers for outputs of a vessel wall, calcium, soft plaque, and liquid blood corresponding to classifications of inputs 810 of various wavelengths (650, 540, 490 and 398) detected. Based on the maximum vessel size and photoacoustic spatial resolution calculations, a 9 mm cube with 30×30×30 voxels is sufficient to cover most PAD clinical scenarios. With 4 wavelengths this leads to 4×27K voxel volumes, which can be merged into a single 108K voxel volume. With 4 different classifier outputs, each operates 4 completely independent 3D CNN 800 that each has one of the classifier outputs. In various exemplary embodiments, the first convolutional layers of the 3D CNN 800 may be configured to have similar weights. Thus the different classifiers can share the same front end convolutional layers and also differentiate into separate networks deeper into the system. This can result in saving considerable computational resources. In this application, the cropping of the data to only the photoacoustic region of interest can be performed automatically. In comparison, there is no need to have a large light source but instead, emanate light from a small optical aperture at the tip of the catheter. For the UV therapy beam, this light is immediately completely absorbed at the center of the region of interest and creates an acoustic point source that can be unambiguously located by the imaging probe. Of course, other network architectures could also be considered. For example, instead of concatenating the voxels for the different wavelengths into one input signal, one could have a network with multiple volume inputs, one for each wavelength. The output classes may vary as well, one could, for example, have an output indicating the confidence of the tip not pointing at a vessel wall In FIG. 8, the observed photoacoustic signal is shaped by a multitude of interacting factors that are tissue-dependent but not easily captured in a mathematical model. The pattern detection/classification can be performed with a deep 3D convolutional neural network (CNN). In an exemplary embodiment, 3D photoacoustic volumes on the prostate were collected at 5 different wavelengths (760, 800, 850, 930 and 970 nm), and processed using a deep 3D convolutional network to detect cancerous tissue. The volumetric data was cropped to a region of interest encapsulating the suspicious lesions, and the 5 volumes were concatenated to form a single larger 3D volume. The 3D CNN had only the concatenated 3D volume as input, and one binary classifier as output.

In the various exemplary embodiments, the main components of the laser atherectomy system include the atherectomy laser system. For example, a CVX-300™ system retrofitted to add additional pulsed wavelength or the next-generation NEXCIMER® system with the ability to incorporate added wavelengths in a modular manner. The ultrasound system, a set of current transducers added with a photoacoustic receive-only mode. A modified transducer (e.g. optimized for the specific frequency of the photoacoustic response). A trigger line from an atherectomy laser to the ultrasound machine. The laser atherectomy system configured with a wire-based connection, or a wireless connection, and an intelligent solution with an analysis algorithm. The analysis algorithm can be modeled using deep learning for tissue classification based on a photoacoustic image. The processes for implementing the atherectomy laser system provide for user or system feedback, where the user feedback is closed-loop system feedback.

In various exemplary embodiments, the types of user feedback can include the following: the detection of vessel wall tissue at the ablation site can indicate a risk of vessel rupture with further treatment; the detection of liquid blood may be a sign that not enough saline is being flushed during therapy (also increasing vessel rupture risk); the detection of calcium-rich occlusions may necessitate slower advancement of the catheter. The detection of the above conditions can be visually communicated to the user, as an example, by the overlay on top of the B-mode image from the ultrasound machine. Alternatively, the condition can be communicated via an audible alarm signal that could sound and the alert would cause the user to be cautious in proceeding with therapy.

In the various exemplary embodiments, multiple types of closed-loop system feedback can be configured in the laser atherectomy system that includes enabling a clinician to directly control aspects of the laser; enabling directly modulating the laser based on detected tissue type at ablation location, including switching off the laser when vessel wall or liquid blood is detected; and automatically pause treatment when the photoacoustic imaging probe position needs to be adjusted. Further exemplary embodiments can include mechanizing and controlling additional therapy components; adjusting robotically controlled advancement speed of the laser atherectomy system; automatically adjusting the rotation to maximize debulking efficiency; detecting proper saline flush and adjust when needed, and detecting when all occlusion material is removed (i.e. is the lesion removed completely?).

The CVX-300 and NEXCIMER® laser systems can be enabled to utilize both a UV laser (treating tissue) and secondary low-power red laser (a visible indicator of successful connection to the system). Having two or more light sources coupled into the same catheter is already built into the existing optics of the laser system. The modular add-on of additional sources both from a system design standpoint and regulatory. The NEXCIMER® Laser System is designed to accommodate future modifications.

Figure 9:
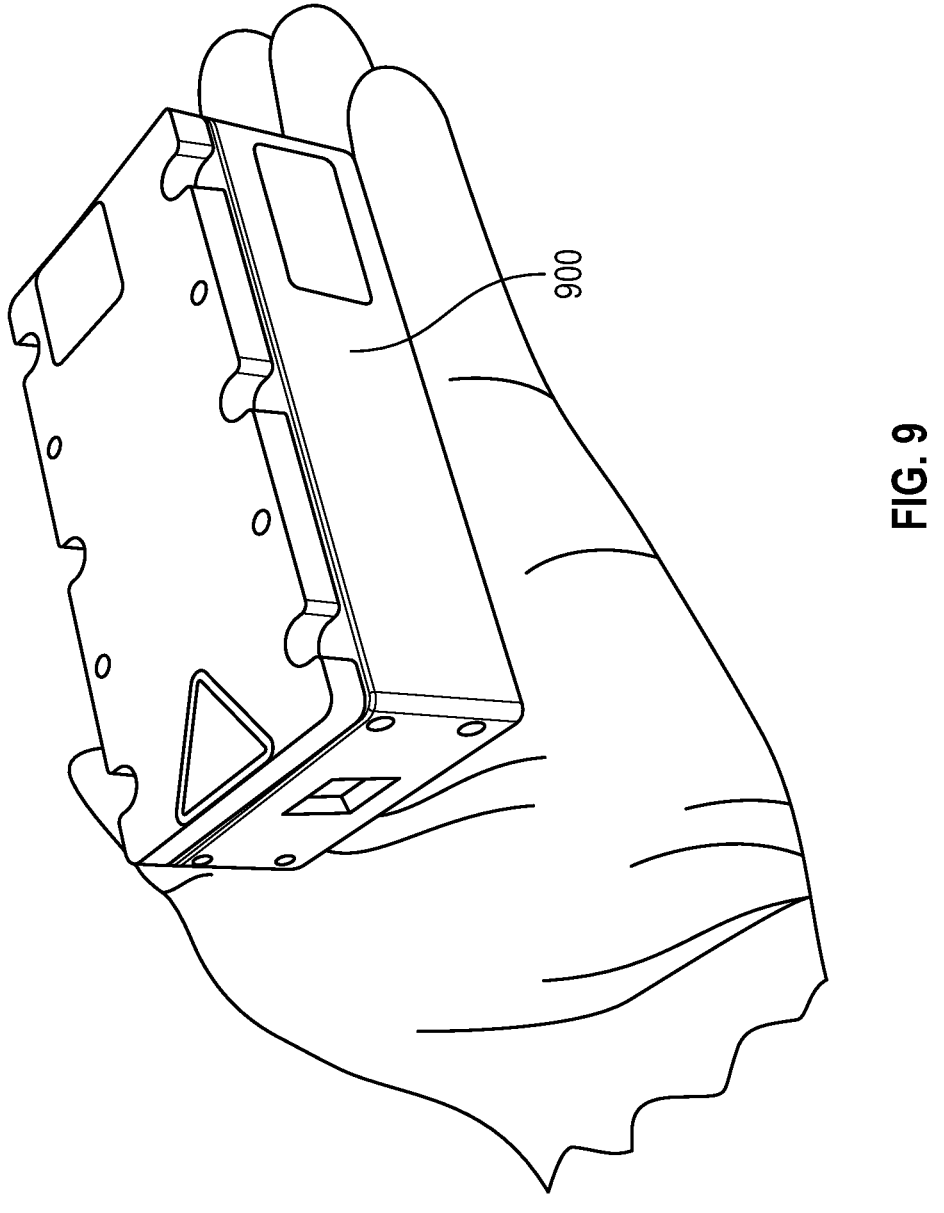
FIG. 9 depicts exemplary laser diodes for use in the photoacoustic imaging probe of the atherectomy laser system in accordance with one or more exemplary embodiments.

FIG. 9 depicts exemplary laser diodes for use in the photoacoustic imaging probe of the atherectomy laser system. The laser diode module 900 provides imaging techniques that combine pulsed laser light for excitation of tissues and an ultrasound transducer as a receptor. The use of ultra-short pulse emission with highly efficient laser diodes in the near-infrared range has been enabled by laser diodes manufactured by QUANTEL®. The multi-wavelength laser source as small as a hand emitted more than 1 mJ per wavelength with four different wavelengths available in pulses of about 90 ns. The laser source can be integrated into high sensitivity photoacoustic handheld systems due to their outstanding electrical-to-optical efficiency of about 25%. Further implementations enable the decrease of the pulse length as low as 40 ns while increasing the pulse energy to 2 mJ. The Laser diode-based illuminators can be configured within 4 wavelength module 900 which is a single wavelength original equipment manufacturer (OEM) module. The module is compact with 4 wavelengths integrated into a single module, and without additional lensing have a beam divergence less than 12 degrees.

Various exemplary embodiments can be configured for the NEXCIMER® Laser System to accommodate future modifications. This is because the hardware is designed in a modular manner with additional slots that are available for the addition of new modules. For expansions to the NEXCIMER® Laser System, the expansions can easily be configured with the additional slots to enable the expanded functionality of the laser. For example, the expansions may include added communications to an exemplary PHILIPS® imaging systems such as C-arms, ultrasound systems, etc. Additionally, telemetry functionality may also be implemented to the NEXCIMER® Laser System. Each of the additional modifications can be validated in part without having to fully validate the entire ecosystem. Each modification, to the exemplary NEXCIMER® laser System, can be a modular add on to the core systems e.g. as an upgrade to existing systems and be upgraded locally at the device location (out in the field). Also, various levels of add-ons can be configured like regular or a premium add-on that couples the laser system with an exemplary PHILIPS® ultrasound device. The module would be independent of a base laser model function (UV light generation and delivery) within the existing enclosure.

Figure 10:
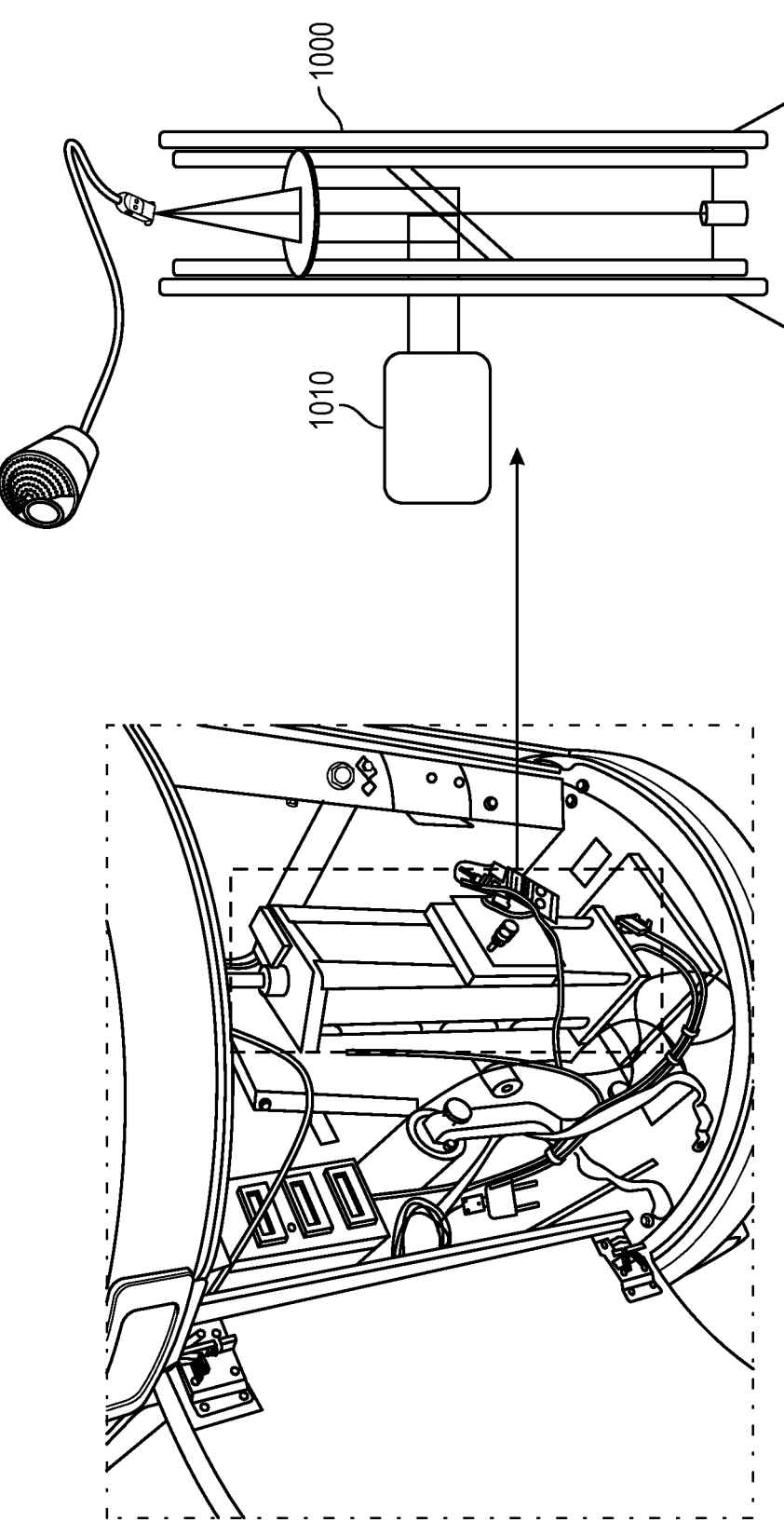
FIG. 10 illustrates the optical rail assembly inside an exemplary laser unit of the atherectomy laser system in accordance with one or more exemplary embodiments.

FIG. 10 illustrates the optical rail assembly 1000 inside an exemplary SPECTRANETICS® CVX-300™ laser unit. In this case, the UV laser unit 1010 is positioned horizontally and produces a large rectangular collimated beam. A dichroic mirror is placed at 45 degrees to deflect this beam upward, where it passes through a lens and gets focused on the entry aperture of the Atherectomy catheter. The dichroic mirror acts as a reflective mirror for the short UV wavelength but is transparent for lower wavelengths. The red laser is similar to a regular laser pointer, sits at the bottom of the optical rail (red box), and shines upward through the mirror and lens, onto the catheter aperture. As the QUANTEL® laser diodes have a lightly diverging beam, hence the laser diodes can be position at the bottom of the optical rail assembly 1000, and at a distance where the beam has diverged sufficiently put a lens to roughly collimate the beam at a diameter similar to the UV optical path so that the same upper lens focusing the UV beam also focusses the other wavelengths at the right spot. In the modularized NEXCIMER® laser system the red indicator light module would simply be replaced with another model incorporating both the added pulsed wavelengths and the red indicator light.

FIG. 11 is an exemplary flowchart 1100 of the endoscopic procedure for operating the laser atherectomy system. At 1105, a task for configuring the atherectomy laser device in combination with an atherectomy catheter for guidance by feedback from photoacoustic images based on the photoacoustic signals generated by the atherectomy laser device directed at the anatomical condition within the vessel at the locality of the anatomical condition in treating the anatomical condition by performing of tissue ablation. At 1110, a task for enabling an endoscopic procedure by using an atherectomy laser device with an atherectomy catheter and combining a photoacoustic ultrasound imaging probe. At 1115, a task for guiding the atherectomy laser device in a vessel to perform the endoscopic atherectomy procedure by providing feedback via photoacoustic images of the use of the atherectomy laser device while the atherectomy laser device is operating within the vessel at a locality of an anatomical condition during the endoscopic atherectomy procedure. At 1120, a task for generating photoacoustic images by the ultrasound imaging probe from photoacoustic signals produced by the atherectomy laser device when performing tissue ablation directed to the anatomical condition. At 1125, a task for detecting by the ultrasound imaging probe operating in combination with the atherectomy laser device, measurements of the photoacoustic signals responsive to the guidance of the atherectomy laser device within the vessel. At 1130, a task for producing measurements of the photoacoustic signals that show the atherectomy laser device's movement and of tissue ablation occurring at the locality of the anatomical condition within the vessel. At 1135, a task for classifying the measurements of the photoacoustic signals using an intelligent solution, into a set of labeled features related to the anatomical condition to guide control of the atherectomy laser device's movement and an amount of tissue ablation during the treatment of the anatomical condition in the endoscopic atherectomy procedure. At 1140, a task for applying an intelligent solution of a neural network model to classify measurements of the photoacoustic signals generated by the atherectomy laser device and directed to the anatomical condition within the vessel. At 1145, a task for detecting, by the ultrasound imaging probe, acoustic intensity of the photoacoustic signals that are used to generate the photoacoustic images. For example, in response to acoustic waves of different acoustic intensity due to different optical wavelengths, emanating from the volume near the catheter tip and received by the ultrasound imaging probe, at a display device in communication with the ultrasound imaging probe, a set of photoacoustic images can be generated with the photoacoustic images having a set of labels of different anatomical features at the therapeutic region. The set of labels are classified using an intelligent solution based on an acoustic wavelength that includes: a vessel wall, liquid blood, amounts of calcium, and composition of the plaque within the vessel; and in response to the labeled different anatomical features generated in the small volume around the atherectomy laser devices' catheter tip, provides a display to users about the orientation of a catheter in a vessel lumen. At 1150, a task for modulating the strength of the acoustic wave for therapy feedback to adjust the ablation capability of the atherectomy laser device. At 1155, a task for classifying, by the ultrasound imaging probe, by changes in the acoustic intensity due to the optical wavelength that characterizes tissue (in addition to optical scattering and attenuation effects that create a spatial "blob" type volume with unique shape signature). Hence, the photoacoustic signal is an ultrasound signal, that is generated by an optical pulse. The wavelength of the ultrasound signal is somewhat related to the duration of the optical pulse but not dependent on the optical wavelength. In practice, the optical pulse has fixed duration. The optical wavelength is changed and the change in intensity of the resulting acoustic signal is recorded by the ultrasound probe (for a range of locations in the imaging volume). At 1160, a task for adjusting the atherectomy laser device's movement in combination with an atherectomy catheter based on guidance from the feedback of the photoacoustic signals generated by the atherectomy laser device within the vessel at the locality of the anatomical condition when treating the anatomical condition by performing tissue ablation.

For the sake of brevity, conventional techniques related to laser atherectomy, and other functional aspects of the subject matter may not be described in detail herein. Also, certain terminology may be used in the herein for reference only, and thus is not intended to be limiting. For example, terms such as "first," "second," and other such numerical terms referring to structures do not imply a sequence or order unless clearly indicated by the context. The foregoing description may also refer to elements or nodes or features being "connected" or "coupled" together. As used herein, unless expressly stated otherwise, "coupled" means that one element/node/feature is directly or indirectly joined to (or directly or indirectly communicates with) another element/node/feature, and not necessarily mechanically.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. For example, the subject matter described herein is not limited to the infusion devices and related systems described herein. Moreover, the foregoing detailed description will provide those skilled in the art with a convenient road map for implementing the described embodiment or embodiments. It should be understood that various changes can be made in the function and arrangement of elements without departing from the scope defined by the claims, which includes known equivalents and fore-seeable equivalents at the time of filing this patent application. Accordingly, details of the exemplary embodiments or other limitations described above should not be read into the claims absent a clear intention to the contrary.

What is claimed is:

1. A method of operating a laser atherectomy system, the method comprising:

performing an endoscopic atherectomy procedure within a vessel at a therapeutic region of an anatomical condition by use of an atherectomy laser device in combination with an ultrasound imaging probe, the atherectomy laser device operating to generate a plurality of photoacoustic signals from a light source of the atherectomy laser device about the therapeutic region by delivery of pulsed wavelengths within the vessel at the therapeutic region, and to perform operations of tissue ablation directed to the anatomical condition;

guiding the atherectomy laser device operating within the vessel with feedback provided by photoacoustic images which are generated by the ultrasound imaging probe based on a plurality of photoacoustic signals that have been generated by the atherectomy laser device while the atherectomy laser device is operating at the therapeutic region for the anatomical condition; and in response to the atherectomy laser device's movement in the vessel to within a close distance to the anatomical condition, automatically switching from a B-mode displaying a broader field of view (FOV) of the therapeutic region to a photoacoustic mode displaying a narrower FOV of the therapeutic region.

2. The method of claim 1, further comprising:

configuring the atherectomy laser device with a primary light source and a secondary light source wherein the primary light source is used for performing the tissue ablation and the secondary light source is used for generating photoacoustic signals for the photoacoustic images.

3. The method of claim 1 wherein the photoacoustic mode's narrower FOV displays a region comprising a close-up area of an atherectomy laser device's catheter tip within the vessel for providing a detailed display of different tissue types within the vessel.

4. The method of claim 3, further comprising:

overlaying an image generated in the photoacoustic mode on an image generated in the B-mode wherein the overlaid photoacoustic image is smaller in size than a B-mode image and configured about the close-up area of the atherectomy laser devices' catheter tip.

5. The method of claim 4, wherein the overlaid image can be enabled or disabled during the atherectomy procedure and wherein the overlaid image can be interleaved therebetween during enablement of the photoacoustic and B-mode.

6. The method of claim 5, further comprising:

generating, by the atherectomy laser device, photoacoustic signals of multiple wavelengths of light by the secondary light source for creating a plurality of acoustic waves in a volume near the atherectomy laser device's catheter tip within the vessel to distinguish anatomical features by monitoring acoustic waves by the ultrasound imaging probe.

7. The method of claim 6, further comprising:

in response to acoustic waves from different optical wavelengths emanating from the volume near the catheter tip and monitored by the ultrasound imaging probe, displaying, at a display device in communication with the ultrasound imaging probe, a set of photoacoustic images comprising photoacoustic images with a set of labels of different anatomical features at the therapeutic region wherein the set of labels are classified using an intelligent solution based on changes of acoustic intensity due to a change of optical wavelength that comprises: a vessel wall, liquid blood, amounts of calcium, and composition of the plaque within the vessel; and in response to the labeled different anatomical features generated in the small volume around the atherectomy laser device's catheter tip, providing a display to users about the orientation of a catheter in a vessel lumen.

8. A laser atherectomy apparatus comprising:

an atherectomy laser device coupled to an ultrasound imaging probe to perform an endoscopic atherectomy procedure within a vessel at a therapeutic region for an anatomical condition by use of an atherectomy laser device;

the atherectomy laser device configured to perform a first function using a primary light source to perform tissue ablation for the anatomical condition, and a second function using a secondary light source to generate a plurality of photoacoustic signals for one or more pulsed wavelengths within the vessel at the therapeutic region;

a display configured to present photoacoustic images based on photoacoustic signals generated by the atherectomy laser device's secondary light source that provides user guidance of the atherectomy laser device by viewing the photoacoustic images of the atherectomy laser device operating within the vessel and anatomical features surrounding the atherectomy laser device at the therapeutic region; and in response to the atherectomy laser device's movement in the vessel to within a close distance to the anatomical condition, the atherectomy laser device configured to enable an automatic switch from a B-mode of the display of displaying a broader field of view (FOV) of the therapeutic region to a photoacoustic mode of the display for displaying a narrower FOV of the therapeutic region.

9. The apparatus of claim 8, further comprising:

the display coupled to the atherectomy laser device configured to display for the photoacoustic mode's narrower FOV of a region comprising a close-up area of an atherectomy laser device's catheter tip within the vessel to provide a detailed display of different anatomical features within the vessel for visual guidance of the atherectomy laser device.

10. The apparatus of claim 9, further comprising:

the display configured to overlay an image generated in the photoacoustic mode on an image generated in the B-mode wherein the overlaid photoacoustic image is smaller in size than a B-mode image and configured about the close-up area of the atherectomy laser device's catheter tip.

11. The apparatus of claim 10, wherein the overlaid image can be enabled or disabled during the endoscopic atherectomy procedure.

12. The apparatus of claim 11, further comprising:

the laser atherectomy device configured to generate photoacoustic signals of multiple wavelengths of light by the secondary light source for creating a plurality of acoustic waves for different optical wavelengths in a volume near the atherectomy laser device's catheter tip within the vessel to distinguish anatomical features.

13. The apparatus of claim 12, further comprising:

in response to acoustic waves for different optical wavelengths that emanate from the volume near the catheter tip and monitored by the ultrasound imaging probe, the display device in communication with the ultrasound imaging probe, configured to display a set of photoacoustic images comprising photoacoustic images with labels of different anatomical features at the therapeutic region wherein the labels are classified using an intelligent solution based on changes of acoustic intensity due to a change of optical wavelength.

14. An atherectomy system comprising an atherectomy laser device in communication with an ultrasound imaging probe to display photoacoustic images of an atherectomy procedure, the system comprising:

the atherectomy laser device coupled with an ultrasound imaging probe and configured with a primary light source and a secondary light source to perform the atherectomy procedure by simultaneous or individual use of the primary light source for tissue ablation of an anatomical condition at a therapeutic region discovered in the atherectomy procedure, and by use of a secondary light source to generate a plurality of photoacoustic signals of one or more pulsed wavelengths within the vessel at the therapeutic region which is monitored by the ultrasound imaging probe to create photoacoustic images based on acoustic waves which emanate from photoacoustic signals;

wherein the atherectomy laser device is configured to communicate with the ultrasound imaging probe, and the ultrasound imaging probe is coupled to a display to view photoacoustic images of the atherectomy procedure wherein the photoacoustic signals are generated by the atherectomy laser device's secondary light source and provide user guidance from the view on the display of photoacoustic images in real-time of operations of an atherectomy laser device's movement and tissue ablation within the vessel at the therapeutic region during the atherectomy procedure; and in response to the atherectomy laser device's movement in the vessel to within a close distance to the anatomical condition, the display configured to automatically switch from a display in a B-mode of the ultrasound imaging probe to display a broader field of view (FOV) of the therapeutic region to a display in a photoacoustic mode of the ultrasound imaging probe to display a narrower FOV of the therapeutic region.

15. The atherectomy system of claim 14, wherein the display coupled to the atherectomy laser device displays the photoacoustic mode's narrower FOV of a region comprising a close-up area of an atherectomy laser device's catheter tip to provide a detailed display of different tissue types within the vessel for visual guidance of the atherectomy laser device.

16. The atherectomy system claim 15, further comprising:

the display further configured to:

overlay an image generated in the photoacoustic mode on an image generated in the B-mode wherein the overlaid photoacoustic image is smaller than a B-mode image and configured about the close-up area of the atherectomy laser device's catheter tip.

17. The atherectomy system of claim 16, further comprising:

the laser atherectomy device configured to:

generate photoacoustic signals of multiple wavelengths of light by the secondary light source to create a plurality of acoustic waves in a volume near the atherectomy laser device's catheter tip within the vessel for monitoring by the ultrasound imaging probe to create photoacoustic images with labels of different anatomical features wherein the labels are classified using an intelligent solution based on a change in acoustic intensity due to a change of optical wavelength.

* * * * *